Figure 1:
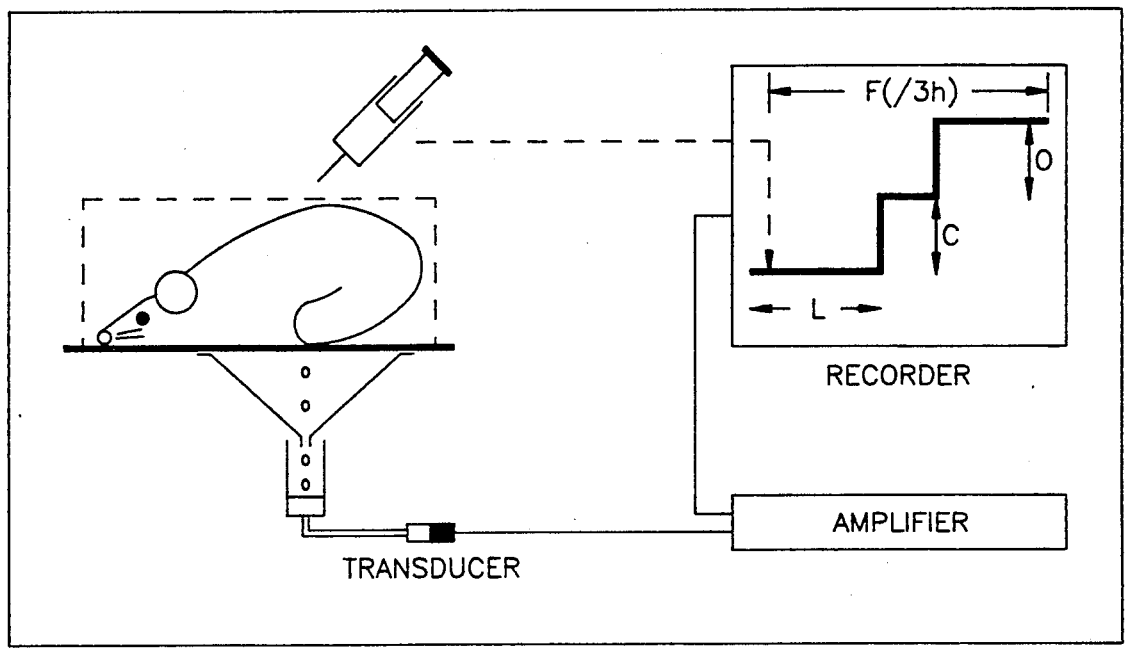

United States Patent [19]

Davis

[11] Patent Number: 5,130,336
[45] Date of Patent: Jul. 14, 1992

[54] METHOD FOR TREATMENT FOR NEURO-MUSCULAR INCONTINENCE

[75] Inventor: William M. Davis, Tucson, Ariz.

[73] Assignee: United Pharmaceuticals, Inc., Tucson, Ariz.

[21] Appl. No.: 792,799

[22] Filed: Nov. 15, 1991

[51] Int. Cl.⁵ ............................................. A61K 31/21
[52] U.S. Cl. .................................................... 514/513
[58] Field of Search ......................................... 514/513

Primary Examiner—S. J. Friedman
Attorney, Agent, or Firm—Austin E. Miller

[57] ABSTRACT

Treating a patient for neuro-muscular incontinence by administering a thiol-S-(2-diethyl-aminoethyl)-ester compound selected from the group consisting of trimethylacetyl-thio-S-(2-diethylaminoethyl)-ester, 1-cyclohexyl-1-phenylacetyl-thiol-S-(2-diethylaminoethyl)-ester, palmitoyl-thio-S-(2-diethylaminoethyl)-ester, 4-t-butyl-benzoyl-thiol-S-(2-diethylaminoethyl)-ester, phenylacetyl-thio-S-(2-diethylaminoethyl)-ester, 4-phenyl-butyryl-thio-S-(2-diethylaminoethyl)-ester, and 2-ethyl-butyryl-thio-S-(2-diethylaminoethyl)-ester.

16 Claims, 2 Drawing Sheets

METHOD FOR TREATMENT FOR NEURO-MUSCULAR INCONTINENCE

BACKGROUND OF THE INVENTION

The present invention relates to a method of treating patients for neuro-muscular incontinence. More particularly, the invention relates to the relief of incontinence created by smooth muscle spasm, and relates to the use of new pharmaceutical compounds having useful antispasmodic properties.

DESCRIPTION OF THE PRIOR ART

It is known to use antispasmodic drugs to relieve spasms of the smooth muscles. As disclosed in my U.S. Pat. No. 4,857,535, granted Aug. 15, 1989, the purpose of an antispasmodic drug is to relieve spasms of the smooth muscles. Such spasms may be due to exaggerated impulses from the parasympathetic branch of the autonomic nervous system or the muscle may be intrinsically stimulated into a spasm, most likely from chemical changes in the surrounding tissue. Atropine may be used to treat spasms due to exaggerated impulses from the parasympathetic branch of the autonomic nervous system (neurotropic effect) while substances such as papaverine have the ability to decrease intrinsically the contractility of the smooth muscle, and has the ability to relax smooth muscles directly by what is called a "musculotropic effect".

U.S. Pat. No. 2,390,555 discloses a class of compounds comprising di-N-substituted aminoethyl esters of diphenylthioacetic acid of the general formula $(C_6H_5)_2$—CH—COS—$CH_2CH_2$—R in which R represents a disubstituted amino radical of either the diethylamino group, the morpholino group or the piperidino group with N as the point of attachment. This patent discloses that the thio analogs of certain disubstituted acetic acid esters of aminoalcohols have desirable antispasmodic properties. These compounds have proven to be very effective and are widely used as antispasmodics without encountering the undesirable side reactions due to excessive neurotropic effect.

U.S. Pat. No. 4,432,977 discloses new uses, especially for the dilation of the smooth muscles of the upper urinary tract, of the compounds disclosed in U.S. Pat. No. 2,390,555.

In *Compte Rendu de la Societe de Biologie*, 140, pp 477-b 9, (1946) Dupre, Levy and Tchoubar disclose a series of compounds having the formula $C_6H_5(R)CH$—$C(O)$—S—$CH_2CH_2N(CH_2CH_3)_2$ where R is either a phenyl group, a propyl group, an isopropyl group, a butyl group or an isoamyl group. These compounds are all disclosed as being spasmolytic agents.

Compounds of the same general formula given above are disclosed by Tchoubar and Letellier-Dupre in *Bulletin de la Societe Chimique*, pp 792-4 (1947) wherein R was a phenyl group, an ethyl group, a propyl group, an isopropyl group, a butyl group, an isoamyl group or hydrogen.

In *Farmakol. i. Toksikol.*, pp 10-17 (1956), Liberman discloses a class of compounds having the general formula $(C_6H_5)_2CHCOSCH_2CH_2N$—$R_2$, wherein both R's are the same and are selected from methyl, ethyl, propyl and butyl groups; and a class of compounds having the general formula $(C_6H_5)$—$CH(C_6H_{11})COSCH_2CH_2N$—$R_2$, wherein both R's are the same and are selected from methyl, ethyl, propyl and butyl groups.

C. A. Buehler et al in the *Journal of Medicinal Chemistry*, 6, pp 230-3 (1963) disclose physiologically active compounds of the general formula $RR'C(OH)$-$COS(CH_2)_xNR_2''$·HCl wherein R and R' are aryl groups, x is 2 or 3, and $R_2''$ is a methyl or ethyl group.

R. O. Clinton et al in the Journal of *the American Chemical Society*, 68, pp 2076-7 (1946) disclose synthesis of a number of dialkyl aminoalkyl diarylthiolacetates including fluorene-9-carbothioic acid, S-[2-diethylaminoethyl]ester.

OBJECTS OF THE INVENTION

It is an object of this invention to provide a new method for treatment for neuro-muscular incontinence, and having a highly useful and effective influence upon the bladder.

Still another object is to provide a new method for enhancing bladder capacity and reducing the voiding frequency.

Still another object of this invention is to provide a rapid and accurate method to evaluate the pharmacologic action of a drug relevant to the urinary tract, which avoids the use of anesthesia and of external infusion into the bladder.

Still another important object of the present invention is to provide a method of treatment for neuro-muscular incontinence by introducing a highly effective agent which is free of undesirable side effects.

Other objects and advantages of this invention will further become apparent hereinafter and in the drawings.

DRAWINGS

In the drawings which are submitted as illustrative but are not intended to define or limit the scope of the invention, FIG. 1 is a schematic diagram illustrating an experimental set up for the measurement of volume evoked micturition reflex (VEMR). The inset shows the principal parameters, wherein L means latency, C means capacity of first micturition volume, and O means total urine produced per period of observation.

Figures 2, 3:
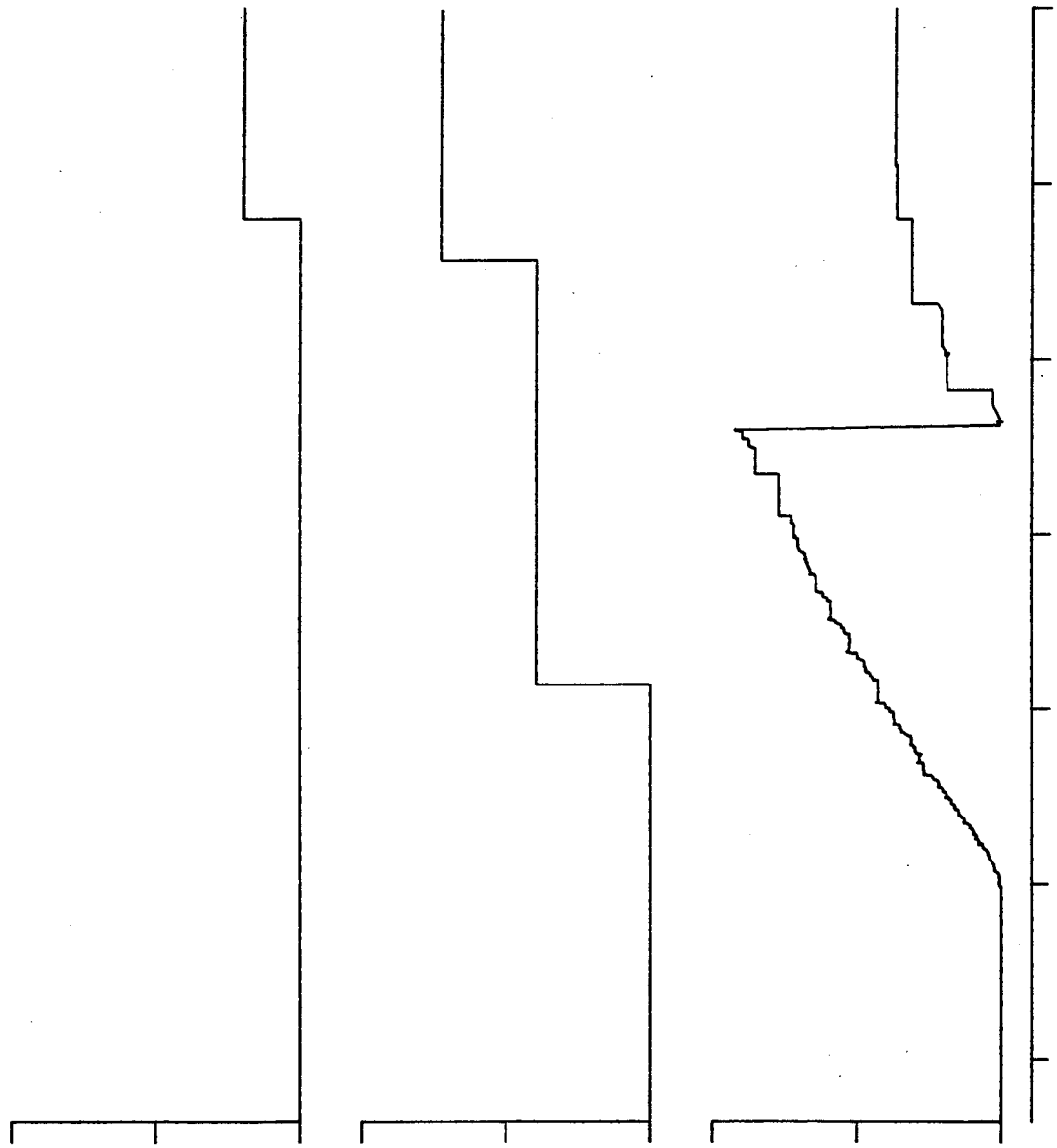

FIG. 2 shows histograms of the distribution of VEMR parameters over a 24-hour period. The circadian rhythm of spontaneous voidings without furosemide is also shown. The mean voided volume for the entire period is also shown. Indicated values are mean ±SE.

FIG. 3 shows typical recording of VEMR showing the characteristic pattern of voiding under different conditions.

SUMMARY OF THE INVENTION

These and other objects are met by administering to a patient suffering from neuro-muscular incontinence a safe and effective amount of a -thio-S-(2-diethylaminoethyl)-ester compound of a radical selected from the group consisting of trimethylacetyl, 1-cyclohexyl-1-phenylacetyl, palmitoyl, 4-t-butyl, phenylacetyl, 4-phenyl-butyryl and 2-ethyl-butyryl. 1-cyclohexyl-1-phenylacetyl-thiol-S-(2-diethylaminoethyl)-ester, for example, has the following formula:

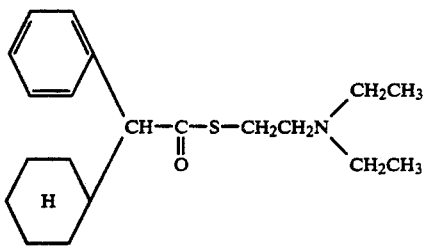

The others of the group have corresponding formulae simply substituting for the 1-cyclohexyl-1-phenylacetyl group the individual moiety selected.

It has now been surprisingly discovered that each of these compounds has a remarkably beneficial effect on the bladder and has positive effect for the treatment of patients for neuro-muscular incontinence. The compound can be administered orally, typically in tablets of 100-400 mg, or by intravenous injection. It is also possible to encapsulate microspheres of the compound in the form of a liquid suspension for administration to patients.

It has further been discovered that the administration of the compound produces larger bladder capacity, tends to produce a significant reduction in the frequency of voidings and, when used in conjunction with furosemide or other diuretic agent achieves a highly useful anti-diuretic effect, and also provides a highly advantageous latency of voidings.

EXAMPLES

The Examples which follow are intended to be illustrative of the invention but are not intended to define or to limit the scope of the invention which is defined in the appended claims.

There is an acute clinical need for the development of drugs and pharmacologic methods that can be used for the identification and rapid evaluation of drugs useful in treating urinary incontinence. The most common condition that can be treated pharmacologically is incontinence due to detrusor instability (DI). Most available drugs increase bladder capacity by suppressing the premature voiding contractions present in DI patients. Such drugs also decrease the frequency of voluntary voiding that is associated with urgency.

To test the efficacy of drugs on DI, pharmacologists use an array of in vitro and in vivo methodologies that range from binding studies and isometric responses to complex urodynamic investigations. The pharmaceutical industry frequently is challenged with performing this quantitative evaluation of a number of drugs that are analogs to each other but possess sharply different specific properties for the treatment of DI. This evaluation should consist of a simple set of parameters so that comparisons can be made to analogs as well as agents currently in clinical use.

In the following Examples, we have, in addition to reporting the results of treatment for neuro-muscular incontinence with the use of the compounds of the invention, tested and reported a multiplicity of comparative compounds.

The screening method used avoids the use of anesthesia and of external infusion into the bladder relying on the physiological stimulation of the VEMR by diuresis.

Mature female Sprague-Dawley rats weighing 240-310 gm were placed in restrainer cages (Braintree Scientific, Inc., Mass.) which afforded access to food and water. Some limited lateral and back and forth movement was allowed in the cages. Under the rear of the rat a collecting funnel and weight measuring device was secured. The collector was secured to a Statham UC3 strain transducer, the output of which was amplified by a Gould bridge amplifier. Data collected were monitored on a Gould 2400 polygraph. For each VEMR, the weight of the volume voided, and the time of voiding were recorded on the polygraph.

To evaluate the relative pharmacologic efficacy of each drug under study, 1 mg/kg furosemide along with the drug to be evaluated was diluted in 5 ml of saline and injected subcutaneously.

In baseline studies the bladder capacity for each voiding varies in a circadian manner. Consistent bladder capacities were obtained with the addition of furosemide.

Rats received approximately equimolar concentrations ($2.8 \times 10^{-3}$M) of analogs to the compounds of the invention. To establish a standard of comparison, test drugs representing $Ca^{++}$ blocking, anticholingerics and a $K^+$ channel opener were also examined.

This method (subcutaneous injection of a fluid and diuretic load simultaneously with a pharmacologic agent) proved an accurate and reproducible means of eliciting VEMR. This model allows rapid evaluation of various drugs designed to increase bladder capacity and decrease the frequency of voiding. It is particularly useful in evaluating the relative efficacy of drugs that are chemical analogs.

This method is based on the evaluation of the voiding parameters provided by the VEMR which has itself been extensively studied. (Durant et al 1988; Durant and Yaksh 1988a, 1988b; Sosnowski and Yaksh 1990). The drugs studied were compared with other drugs that are currently under investigation. The advantage of this test these drugs is that it avoids all surgical interventions, minimizes the number of animals used, and can be used on a relatively large scale. It is also possible to make comparisons using a single dose and thus test the efficacy of action in a wide variety of drugs.

TEST METHOD

Baseline Studies

With this set-up, urine output, frequency, volume per micturition and micturition time were monitored for any 24-hour period. Experiments were then performed from 9:00 a.m. to the same the next day in order to establish the circadian VEMR values. Baseline values of micturition frequency, volume and output, initially measured over a 24-hour period, showed a wide variation in volume voided and diuresis. The method was thus modified to produce a more reliable diuretic load that is not dependent on the circadian rhythm.

Controls

To evaluate the pharmacologic efficacies of the various drugs under study, a single subcutaneous injection of a 5 ml saline fluid load with 1 mg/kg furosemide was initially given to rats to establish the control values of the parameters measured.

Study Animals

To obtain a controlled amount of diuresis and avoid circadian variations in urine flow, 1 mg/kg furosemide and 5 ml of saline were added to each drug under study.

VEMR were observed for three hours as a rule, except in instances were the latency was more than three hours. On such occasions the period of recording is indicated specifically in the results. The parameters of VEMR considered in this study are defined as follows:

$V_o$: volume voided on first micturition
V: mean volume voided during entire study period
D: diuretic effect over entire study period
F: frequency of micturition
L: latency period from time of injection to first micturition.

In addition to the quantitative data obtained for the parameters given above, the pattern of micturition was qualitatively identified, particularly the incidence of dribbling.

Tests were done using (1) baseline—no drug, (2) control—furosemide, (3) atropine (1 mg/kg), (4) oxybutinin (18 mg/kg), (5) terodiline (1.5 mg/kg), (6) diltiazem (18 mg/kg), (7) lamakalim (0.016 mg/kg), (8) urecholine, and the drugs listed:

COMPOUNDS ACCORDING TO THIS INVENTION trimethylacetyl-thio-S-(2-diethylaminoethyl)-ester.HCl
1-cyclohexyl-1-phenylacetyl-thiol-S-(2-diethylaminoethyl)-ester.HCl
palmitoyl-thio-S-(2-diethylaminoethyl)-ester.HCl
4-t-butyl-benzoyl-thiol-S-(2-diethylaminoethyl)-ester.HCl
phenylacetyl-thio-S-(2-diethylaminoethyl)-ester.HCl
4-phenyl-butyryl-thio-S-(2-diethylaminoethyl)-ester.HCl
2-ethyl-butyryl-thio-S-(2-diethylaminoethyl)-ester.HCl

COMPARATIVE COMPOUNDS 2-phenyl-butyryl-thio-S-(2-diethylaminoethyl)-ester.HCl
1-naphtylacetyl-thio-S-(2-diethylaminoethyl)-ester.HCl
phenoxyacetyl-thiol-S-(2-diethylaminoethyl)-ester.HCl
4-biphenyl-carboxyl-thiol-S-(2-diethylaminoethyl)-ester.HCl
fluorene-carboxyl-thiol-S-(2-diethylaminoethyl)-ester.HCl
t-butyl-acetyl-thiol-S-(2-diethylaminoethyl-ester.HCl
2-propyl-pentanoyl-thiol-S-(2-diethylaminoethyl)-ester.HCl
adamante-carboxyl-thiol-S-(2-diethylaminoethyl)-ester.HCl

Statistical Methods

Data were compared using ANOVA (analysis of variance model) and values given are expressed as ± standard error.

RESULTS

The results of measured parameters for controls with furosemide (1 mg/kg) together with the listed drugs are shown in Tables 1–5.

TABLE 1

| Volume Voided on First Micturition (Vo) | Vo | ± SE | % C |
|---|---|---|---|
| Compounds According To This Invention | | | |
| Trimethylacetyl-thio-S-(2-diethylaminoethyl)-ester.HCl | 5.30 | .57 | 83 |
| 1-cyclohexyl-1-phenylacetyl-thiol-S-(2-diethylaminoethyl)-ester.HCl | 4.07 | .39 | 41 |
| Palmitoyl-thio-S-(2-diethylaminoethyl)-ester.HCl | 4.27 | .61 | 48 |
| 4-t-butyl-benzoyl-thiol-S-(2-diethylaminoethyl)-ester.HCl | 4.37 | .40 | 51 |
| 4-phenyl-butyryl-thio-S-(2-diethylaminoethyl)-ester.HCl | 4.35 | 1.06 | 51 |
| Phenylacetyl-thio-S-(2-diethylaminoethyl)-ester.HCl | 4.12 | .32 | 42 |
| 2-ethyl-butyryl-thio-S-(2-diethylaminoethyl)-ester.HCl | 4.43 | .94 | 53 |
| Comparative Compounds | | | |
| Baseline (no drug) | • | • | • |
| Control | 2.89 | .48 | 0 |
| Atropine 1 mg/kg | 2.83 | .57 | −2 |
| Oxybutynin | 2.76 | .44 | −4 |
| Terodiline 1.5 mg/kg | 3.57 | .45 | 24 |
| Diltiazem | 3.30 | .51 | 14 |
| Lemakalim 0.16 mg/kg | 4.37 | .38 | 51 |
| Urecholine | 3.40 | .73 | 18 |
| 2-phenyl-butyryl-thio-S-(2-diethylaminoethyl)-ester.HCl | 3.85 | .99 | 33 |
| 1-naphthylacetyl-thio-S-(2-diethylaminoethyl)-ester.HCl | 3.30 | .57 | 14 |
| phenoxyacetyl-thiol-S-(2-diethylaminoethyl)-ester.HCl | 3.82 | .72 | 32 |
| 4-biphenyl-carboxyl-thiol-S-(2-diethylaminoethyl)-ester.HCl | 3.32 | .35 | 15 |
| Fluorene-carboxyl-thiol-S-(2-diethylaminoethyl)-ester.HCl | 2.55 | .35 | −12 |
| t-butyl-acetyl-thiol-S-(2-diethylaminoethyl-ester.HCl | 1.77 | .23 | −39 |
| 2-propyl-pentanoyl-thiol-S-(2-diethylaminoethyl)-ester.HCl | 2.95 | .46 | 2 |
| adamante-carboxyl-thiol-S-(2-diethylaminoethyl)-ester.HCl | 2.95 | .77 | 2 |

Key:
Vo = volume voided on first micturition
± SE = standard of error
% C = percent change from control

TABLE 2

| Mean Volume (V) Voided During Entire Period of Study | V | ± SE | % C |
|---|---|---|---|
| Compounds According To This Invention | | | |
| Trimethylacetyl-thio-S-(2-diethylaminoethyl)-ester.HCl | 5.30 | .57 | 71 |
| 1-cyclohexyl-1-phenylacetyl-thiol-S-(2-diethylaminoethyl)-ester.HCl | 4.07 | .40 | 31 |
| Palmitoyl-thio-S-(2-diethylaminoethyl)-ester.HCl | 4.57 | .53 | 47 |
| 4-t-butyl-benzoyl-thiol-S-(2-diethylaminoethyl)-ester.HCl | 4.32 | .40 | 39 |
| Phenylacetyl-thio-S-(2-diethylaminoethyl)-ester.HCl | 4.33 | .36 | 40 |
| 4-phenyl-butyryl-thio-S-(2-diethylaminoethyl)-ester.HCl | 4.53 | 1.03 | 46 |

TABLE 2-continued

Mean Volume (V) Voided During Entire Period of Study

| | V | ± SE | % C |
|---|---|---|---|
| 2-ethyl-butyryl-thio-S-(2-diethylaminoethyl)-ester.HCl | 4.12 | .70 | 33 |
| Comparative Compounds | | | |
| Baseline (no drug) | • | • | • |
| Control | 3.10 | .41 | 0 |
| Atropine 1 mg/kg | 3.16 | .41 | 2 |
| Oxybutynin | 2.77 | .41 | −11 |
| Terodiline 1.5 mg/kg | 3.62 | .44 | 17 |
| Diltiazem | 3.29 | .51 | 6 |
| Lemakalim 0.16 mg/kg | 4.37 | .40 | 41 |
| Urecholine | 2.84 | .56 | −8 |
| 2-phenyl-butyryl-thio-S-(2-diethylaminoethyl)-ester.HCl | 4.09 | .76 | 32 |
| 1-naphthylacetyl-thio-S-(2-diethylaminoethyl)-ester.HCl | 3.46 | .63 | 12 |
| phenoxyacetyl-thiol-S-(2-diethylaminoethyl)-ester.HCl | 3.98 | .67 | 28 |
| 4-biphenyl-carboxyl-thiol-S-(2-diethylaminoethyl)-ester.HCl | 3.32 | .35 | 7 |
| Fluorene-carboxyl-thiol-S-(2-diethylaminoethyl)-ester.HCl | 2.55 | .35 | −18 |
| t-butyl-acetyl-thiol-S-(2-diethylaminoethyl)-ester.HCl | 2.45 | .26 | −21 |
| 2-propyl-pentanoyl-thiol-S-(2-diethylaminoethyl)-ester.HCl | 2.90 | .49 | −6 |
| adamante-carboxyl-thiol-S-(2-diethylaminoethyl)-ester.HCl | 2.97 | .77 | −4 |

Key:
V = mean volume
± SE = standard of error
% C = percent change from control

TABLE 3

Diuretic Effect (D) Over Entire Study

| | D | ± SE | % C |
|---|---|---|---|
| Compounds According To This Invention | | | |
| Trimethylacetyl-thio-S-(2-diethylaminoethyl)-ester.HCl | 5.30 | .47 | −45 |
| 1-cyclohexyl-1-phenylacetyl-thiol-S-(2-diethylaminoethyl)-ester.HCl | 4.07 | .39 | −58 |
| Palmitoyl-thio-S-(2-diethylaminoethyl)-ester.HCl | 6.67 | 1.07 | −31 |
| 4-t-butyl-benzoyl-thiol-S-(2-diethylaminoethyl)-ester.HCl | 4.93 | .62 | −49 |
| Phenylacetyl-thio-S-(2-diethylaminoethyl)-ester.HCl | 6.85 | 1.45 | −29 |
| 4-phenyl-butyryl-thio-S-(2-diethylaminoethyl)-ester.HCl | 6.50 | 1.63 | −33 |
| 2-ethyl-butyryl-thio-S-(2-diethylaminoethyl)-ester.HCl | 7.13 | .94 | −26 |
| Comparative Compounds | | | |
| Baseline (no drug) | • | • | • |
| Control | 9.67 | 2.11 | 0 |
| Atropine 1 mg/kg | 4.78 | .61 | −51 |
| Oxybutynin | 4.20 | .90 | −57 |
| Terodiline 1.5 mg/kg | 4.12 | .56 | −57 |
| Diltiazem | 3.90 | .80 | −60 |
| Lemakalim 0.16 mg/kg | 4.37 | .38 | −55 |
| Urecholine | 10.72 | 2.53 | 11 |
| 2-phenyl-butyryl-thio-S-(2-diethylaminoethyl)-ester.HCl | 8.00 | 1.16 | −17 |
| 1-naphthylacetyl-thio-S-(2-diethylaminoethyl)-ester.HCl | 5.70 | 1.67 | −41 |
| phenoxyacetyl-thiol-S-(2-diethylaminoethyl)-ester.HCl | 6.00 | .80 | −38 |
| 4-biphenyl-carboxyl-thiol-S-(2-diethylaminoethyl)-ester.HCl | 3.32 | .35 | −66 |
| Fluorene-carboxyl-thiol-S-(2-diethylaminoethyl)-ester.HCl | 2.55 | 3.50 | −74 |
| t-butyl-acetyl-thiol-S-(2-diethylaminoethyl)-ester.HCl | 5.52 | .41 | −43 |
| 2-propyl-pentanoyl-thiol-S-(2-diethylaminoethyl)-ester.HCl | 5.73 | .72 | −41 |
| adamante-carboxyl-thiol-S-(2-diethylaminoethyl)-ester.HCl | 3.22 | .71 | −67 |

Key:
D = diuretic effect
± SE = standard of error
% C = percent change from control

TABLE 4

Frequency of Micturition (F) Over Entire Recording Period

| | F | ± SE | % C |
|---|---|---|---|
| Compounds According To This Invention | | | |
| Trimethylacetyl-thio-S-(2-diethylaminoethyl)-ester.HCl | 1.00 | 0 | −66 |
| 1-cyclohexyl-1-phenylacetyl-thiol-S-(2-diethylaminoethyl)-ester.HCl | 1.00 | 0 | −66 |
| Palmitoyl-thio-S-(2-diethylaminoethyl)-ester.HCl | 1.50 | .22 | −49 |
| 4-t-butyl-benzoyl-thiol-S-(2-diethylaminoethyl)-ester.HCl | 1.17 | .17 | −60 |
| Phenylacetyl-thio-S-(2-diethylaminoethyl)-ester.HCl | 1.50 | .22 | −49 |
| 4-phenyl-butyryl-thio-S-(2-diethylaminoethyl)-ester.HCl | 1.50 | .29 | −49 |
| 2-ethyl-butyryl-thio-S-(2-diethylaminoethyl)-ester.HCl | 1.83 | .17 | −37 |
| Comparative Compounds | | | |
| Baseline (no drug) | • | • | • |
| Control | 2.92 | .38 | 0 |
| Atropine 1 mg/kg | 1.67 | .33 | −43 |
| Oxybutynin | 1.50 | .19 | −49 |
| Terodiline 1.5 mg/kg | 1.17 | .17 | −60 |
| Diltiazem | 1.17 | .17 | −60 |

TABLE 4-continued

Frequency of Micturition (F) Over Entire Recording Period

|  | F | ± SE | % C |
|---|---|---|---|
| Lemakalim 0.16 mg/kg | 1.00 | 0 | −66 |
| Urecholine | 3.67 | .33 | 26 |
| 2-phenyl-butyryl-thio-S-(2-diethylaminoethyl)-ester.HCl | 2.25 | .63 | −23 |
| 1-naphthylacetyl-thio-S-(2-diethylaminoethyl)-ester.HCl | 1.50 | .22 | −4 |
| phenoxyacetyl-thiol-S-(2-diethylaminoethyl)-ester.HCl | 1.70 | .33 | −42 |
| 4-biphenyl-carboxyl-thiol-S-(2-diethylaminoethyl)-ester.HCl | 1.00 | 0 | −66 |
| Fluorene-carboxyl-thiol-S-(2-diethylaminoethyl)-ester.HCl | 1.00 | 0 | −66 |
| t-butyl-acetyl-thiol-S-(2-diethylaminoethyl)-ester.HCl | 2.33 | .21 | −20 |
| 2-propyl-pentanoyl-thiol-S-(2-diethylaminoethyl)-ester.HCl | 2.17 | .31 | −26 |
| adamante-carboxyl-thiol-S-(2-diethylaminoethyl)-ester.HCl | 1.17 | .17 | −60 |

Key:
F = frequency of micturition
± SE = standard error
% C = percent change from control

TABLE 5

Latency Period (Lo) From the Time of Injection

|  | Lo | ± SE | % C |
|---|---|---|---|
| Compounds According To This Invention | | | |
| Trimethylacetyl-thio-S-(2-diethylaminoethyl)-ester.HCl | 36.8 | 4.4 | 57 |
| 1-cyclohexyl-1-phenylacetyl-thiol-S-(2-diethylaminoethyl)-ester.HCl | 132.2 | 25.2 | 463 |
| Palmitoyl-thio-S-(2-diethylaminoethyl)-ester.HCl | 36.7 | 2.2 | 56 |
| 4-t-butyl-benzoyl-thiol-S-(2-diethylaminoethyl)-ester.HCl | 60.5 | 16.5 | 157 |
| Phenylacetyl-thio-S-(2-diethylaminoethyl)-ester.HCl | 53.8 | 18.9 | 129 |
| 4-phenyl-butyryl-thio-S-(2-diethylaminoethyl)-ester.HCl | 27.5 | 2.1 | 17 |
| 2-ethyl-butyryl-thio-S-(2-diethylaminoethyl)-ester.HCl | 25.8 | 2.2 | 10 |
| Comparative Compounds | | | |
| Baseline (no drug) | • | • | • |
| Control | 23.5 | 8.8 | 0 |
| Atropine 1 mg/kg | 33.7 | 4.8 | 43 |
| Oxybutynin | 50.4 | 7.5 | 114 |
| Terodiline 1.5 mg/kg | 94.8 | 26.0 | 303 |
| Diltiazem | 157.5 | 21.9 | 570 |
| Lemakalim 0.16 mg/kg | 37.5 | 3.2 | 60 |
| Urecholine | 11.5 | 1.2 | −51 |
| 2-phenyl-butyryl-thio-S-(2-diethylaminoethyl)-ester.HCl | 31.2 | 3.2 | 33 |
| 1-naphthylacetyl-thio-S-(2-diethylaminoethyl)-ester.HCl | 73.5 | 24.9 | 213 |
| phenoxyacetyl-thiol-S-(2-diethylaminoethyl)-ester.HCl | 25.3 | 1.9 | 8 |
| 4-biphenyl-carboxyl-thiol-S-(2-diethylaminoethyl)-ester.HCl | 106.0 | 41.6 | 351 |
| Fluorene-carboxyl-thiol-S-(2-diethylaminoethyl)-ester.HCl | 130.5 | 43.0 | 455 |
| t-butyl-acetyl-thiol-S-(2-diethylaminoethyl)-ester.HCl | 34.7 | 3.3 | 48 |
| 2-propyl-pentanoyl-thiol-S-(2-diethylaminoethyl)-ester.HCl | 45.7 | 3.9 | 94 |
| adamante-carboxyl-thiol-S-(2-diethylaminoethyl)-ester.HCl | 85.5 | 40.7 | 264 |

Key:
Lo = latency period
± SE = standard of error
% C = percent change from control

TABLE 6

|  | TABLE 1 (1-7) 1ST VOID | TABLE 2 (1-7) MEAN VOL. | TABLE 3 (1-11) DIURETIC VOL. | TABLE 4 (1-7) FREQUENCY | TABLE 5 (1-10) LATENCY | COMPOSITE RANK TABLES 1-4 | COMPOSITE RANK TABLES 1-5 |
|---|---|---|---|---|---|---|---|
| Part I — COMPOSITE RANKS OF COMPOUNDS ACCORDING TO THIS INVENTION | | | | | | | |
| trimethylacetyl-thio-S-(2-diethylaminoethyl)-ester.HCl | 1 | 1 | 6 | 1 | 8 | 1 | 2 |
| 1-cyclohexyl-1-phenylacetyl-thiol-S-(2-diethylaminoethyl)-ester.HCl | 3 | 3 | 8 | 1 | 2 | 3 | 1 |
| palmitoyl-thio-S-(2-diethylaminoethyl)-ester.HCl | 2 | 2 | 4 | 3 | 8 | 2 | 4 |
| 4-t-butyl-benzoyl-thiol-S-(2-diethylaminoethyl)-ester.HCl | 2 | 2 | 6 | 2 | 6 | 3 | 3 |
| phenylacetyl-thio-S-(2-diethylaminoethyl)-ester.HCl | 3 | 2 | 4 | 3 | 6 | 3 | 3 |
| 4-phenyl-butyryl-thio-S-(2-diethylaminoethyl)-ester.HCl | 2 | 2 | 4 | 3 | 9 | 2 | 5 |
| 2-ethyl-butyryl-thio-S-(2-diethylaminoethyl)-ester.HCl | 2 | 3 | 3 | 4 | 9 | 3 | 6 |
| Part II — Composite Ranks of Comparative Compounds | | | | | | | |
| 2-phenyl-butyryl-thio-S-(2-diethylaminoethyl)-ester.HCl | 4 | 3 | 2 | 5 | 8 | 5 | 7 |

TABLE 6-continued

| | TABLE 1 (1-7) 1ST VOID | TABLE 2 (1-7) MEAN VOL. | TABLE 3 (1-11) DIURETIC VOL. | TABLE 4 (1-7) FREQUENCY | TABLE 5 (1-10) LATENCY | COMPOSITE RANK TABLES 1-4 | COMPOSITE RANK TABLES 1-5 |
|---|---|---|---|---|---|---|---|
| 1-naphthylacetyl-thio-S-(2-diethylaminoethyl)-ester.HCl | 5 | 5 | 5 | 3 | 5 | 7 | 8 |
| phenoxyacetyl-thiol-S-(2-diethylaminoethyl)-ester.HCl | 4 | 4 | 5 | 4 | 9 | 6 | 10 |
| 4-biphenyl-carboxyl-thiol-S-(2-diethylaminoethyl)-ester.HCl | 5 | 5 | 10 | 1 | 3 | 9 | 9 |
| fluorene-carboxyl-thiol-S-(2-diethylaminoethyl)-ester.HCl | 6 | 6 | 11 | 1 | 2 | 12 | 10 |
| t-butyl-acetyl-thiol-S-(2-diethylaminoethyl-ester.HCl | 7 | 7 | 5 | 5 | 8 | 12 | 14 |
| 2-propyl-pentanoyl-thiol-S-(2-diethylaminoethyl)-ester.HCl | 6 | 6 | 5 | 5 | 7 | 13 | 15 |
| adamante-carboxyl-thiol-S-(2-diethylaminoethyl)-ester.HCl | 6 | 6 | 10 | 2 | 4 | 12 | 11 |

Volume Voided on First Micturition

Table 1 lists the volume voided on first micturition ($V_o$) by the study animals after injection with the listed drug. In evaluating the pharmacologic efficacy of these drugs in the treatment of UI an increase in the volume voided on first micturition is important. A higher volume on first micturition indicates the drug's effectiveness in allowing the bladder to store fluid prior to micturition, thus eliminating the urgency symptomatic of UI.

Clearly, trimethylacetyl-thio-S-(2-diethylaminoethyl)-ester.HCl exhibits exceptional performance in this effect, allowing a volume on first micturition 83% higher than that exhibited by study animals in the control group. Also providing excellent performance are 4-phenyl-butyryl-thio-S-(2-diethylaminoethyl)-ester.HCl, 2-ethyl-butyryl-thio-S-(2-diethylaminoethyl)-ester.HCl, and 4-t-butyl-benzoyl-thiol-S-(2-diethylaminoethyl)-ester.HCl, each inducing a volume on first micturition at least 50% higher than that exhibited by the control group.

Mean Volume Voided During Study Period

Table 2 lists the mean volume voided by the control animals during the entire study period for each drug tested. Similar to the volume voided on first micturition, a high mean volume voided during the period of study is preferred. Again, trimethylacetyl-thio-S-(2-diethylaminoethyl)-ester.HCl exhibits outstanding performance in this regard, increasing the mean volume by 71% over the control group.

The mean volume voided during the study period indicates not only the effect of the drug in allowing the bladder to maintain fluid prior to micturition, but is further indicative of the drug's long-term effectiveness. High volume of first micturition is indicative of the effect of the drug in allowing the bladder to maintain fluid. While preferred, this effectiveness may be short-lived or compensated for by high frequency of micturition.

Palmitoyl-thio-S-(2-diethylaminoethyl)-ester.HCl, 4-phenyl-butyryl-thio-S-(2-diethylaminoethyl)-ester.HCl and phenylacetyl-thio-S-(2-diethylaminoethyl)-ester.HCl all exhibit at least a 40% increase in the mean volume. 2-phenyl-butyryl-thio-S-(2-diethylaminoethyl)-ester.HCl exhibits a 39% increase.

Diuretic Effect

Table 3 measures the diuretic effect of the drugs over the entire study period. A minimum diuretic effect is preferred. A drug exhibiting a high diuretic effect will draw water from the body fluid tending to fill the bladder with fluid at a faster rate than normal. This faster filling of the bladder causes a greater frequency of micturition, a symptom of UI. However, a drug which exhibits an anti-diuretic effect tends to prevent the collection of fluid in the bladder. Although this may diminish frequency, urgency (the tendency for a VEMR to occur prior to having a full bladder) may not be alleviated by administration of the drug. Hence, a drug which exhibits an anti-diuretic effect is generally not desirable for the treatment of UI.

Compounds exhibiting low or moderate diuretic effect were 2-phenyl-butyryl-thio-S-(2-diethylaminoethyl)-ester.HCl, 2-ethyl-butyryl-thio-S-(2-diethylaminoethyl)-ester.HCl phenylacetyl-thio-S-(2-diethylaminoethyl)-ester.HCl, palmitoyl-thio-S-(2-diethylaminoethyl)-ester.HCl and 4-phenyl-butyryl-thio-S-(2-diethylaminoethyl)-ester.HCl.

TABLE 4

Table 4 measures the frequency of micturition over the entire recording period. High frequency of micturition is the symptom most bothersome to the patients suffering UI. Therefore, decrease in micturition frequency is important.

However, changes in frequency upon administration of a drug cannot be viewed in a vacuum. A decrease in frequency brought about by a drug exhibiting anti-diuretic effect is not preferred for the reasons stated above.

Trimethylacetyl-thio-S-(2-diethylaminoethyl)-ester.HCl, 1-cyclohexyl-1-phenylacetyl-thiol-S-(2-diethylaminoethyl)-ester.HCl, 2-ethyl-butyryl-thio-S-(2-diethylaminoethyl)-ester.HCl, and Urecholine all exhibited a 66% decrease in frequency of micturition over the control group. Adamante-carboxyl-thiol-S-(2-diethylaminoethyl)-ester.HCl and 4-t-butyl-benzoyl-thiol-S-(2-diethylaminoethyl)-ester.HCl also proved effective in reducing frequency, showing a reduction of 60% but the drugs outside the scope of this invention were found lacking in other respects.

TABLE 5

Table 5 indicates the latency period, the period of time between ingestion of a fluid volume and initial micturition. Preferably this time period should be long, indicating the potential for low frequency of micturition.

However, of the two statistics, change in frequency is better indicative of the drug's performance in the treatment of UI. Measurements of latency may be inexact in clinical evaluation of the drugs, as patients may ingest fluid volumes at various periods during which the drug is taking effect.

Moreover, like frequency data, latency measurements are susceptible to variations induced by a drug's anti-diuretic effect.

Desirable latency periods were exhibited by 1-cyclohexyl-1-phenylacetyl-thiol-S-(2-diethylaminoethyl)-ester.HCl, 2-ethyl-butyryl-thio-S-(2-diethylaminoethyl)-ester.HCl, 4-biphenyl-carboxyl-thiol-S-(2-diethylaminoethyl)-ester.HCl, adamante-carboxyl-thiol-S-(2-diethylaminoethyl)-ester.HCl and 1-naphthylacetyl-thio-S-(2-diethylaminoethyl)-ester.HCl.

CONCLUSIONS

In summary, five categories of drug activity were measured: frequency, mean volume voided during the observation period, the diuretic effect of the test drug, the volume at first voiding and the latency period between ingestion of the volume load and first micturition. Ideally, a drug utilized in the treatment of UI would exhibit all of the following: greatly decreased frequency, increased mean volume, negligible anti-diuretic effect, large volume upon first voiding and, possibly, increased latency time.

Because these factors do not work independently of each other, certain preferred reactions may be induced and offset by less favorable reactions for other factors. For example, although low frequency an period are preferred, these types of reactions may be artificially induced by a drug which has a high anti-diuretic effect.

For example, 4-biphenyl-carboxyl-thiol-S-(2-diethylaminoethyl)-ester.HCl, adamante-carboxyl-thiol-S-(2-diethylaminoethyl)-ester.HCl and fluorene-carboxyl-thiol-S-(2-diethylaminoethyl)-ester.HCl all induce a desirable reduction in frequency of micturition. However, these compounds also induce very high anti-diuretic effects causing low volume urination. Hence, these drugs would have minimum effect on the bladder wall contractions caused by the entrance of small amounts of fluid into the bladder. Moreover, the anti-diuretic effect of these compounds could cause patient discomfort upon administration.

In order to analyze the overall effectiveness of each of the drugs in treatment of UI, the raw data in Tables 1-5 has been subjected to statistical analysis and compiled in Table 6. Data for each factor for each drug administered are compiled on a weighted scale. For example, the raw data for volume of first voiding has been scored on a scale of 1-7, mean volume voided during observation has been scored likewise. The lower a score received for a particular compound, the better the performance exhibited by that compound with respect to that particular factor.

The scores for each factor are then added and the composite scores obtained. The composite scores are then ranked in order of success, again, lower numbers being preferred. These composite rankings are listed in the last two columns of Table 6.

The composite rankings are presented in two columns, the first being a composite rank for scores from volume of first voiding, mean volume, diuretic effect and frequency. The second column also takes latency period into effect. The composite ranks were compiled in this way due to the difficulty in measuring latency term.

As can be seen from Table 6, trimethylacetyl-thio-S-(2-diethylaminoethyl)-ester.HCl, 1-cyclohexyl-1-phenylacetyl-thiol-S-(2-diethylaminoethyl)-ester.HCl, palmitoyl-thio-S-(2-diethylaminoethyl)-ester.HCl, phenylacetyl-thio-S-(2-diethylaminoethyl)-ester.HCl, 4-t-butyl-benzoyl-thiol-S-(2-diethylaminoethyl)-ester.HCl, 4-phenyl-butyryl-thio-S-(2-diethylaminoethyl)-ester.HCl and 2-ethyl-butyryl-thio-S-(2-diethylaminoethyl)-ester.HCl all exhibit low composite ranks whether latency is considered or not. The unusual combined qualities of these compounds rank them separate from the others and demonstrate their positive universal effect in treatment of urinary incontinence.

To the best of my knowledge, the compounds of this invention have not before been suggested for use for the treatment of neuromuscular incontinence much less for the five factors particularly reported in this specification. The article of Buehler et al "Physiologically Active Compounds..." of October 1962 discloses a compound No. 104 appearing in Table 1, but the compound or its synthesis was indicated as something to be desired and that yields were low. Although some of the compounds of Buehler were tested for mydriatic activity and cerebral stimulation, compound 104 was not subjected to tests. Indeed, Buehler attributed activity to the presence of a hydroxyl group rather than a hydrogen group on the alpha-carbon atom. Although I am the inventor of some patents which include the 1-cyclohexyl-1-phenylacetyl-thiol-S-moiety, they do not have the diethylamino moiety attached to the sulfur. For example, different groups attached to the sulfur atom include the Davis Pat. Nos. 4,857,535 and 4,721,783, but neither suggests the remarkable effects obtained in accordance with this invention. I am also the inventor named in U.S. Pat. Nos. 4,707,480 and 4,432,977, which are directed to phenylacetyl moieties attached to the alpha-carbon, as distinguished from phenylcyclohexyl moieties.

It is accordingly highly unexpected, as reported in the specification, the tests reported in the Tables and particularly in the composite scores reported in Table 6, that highly surprising and highly beneficial results were obtained from the particular pharmacological agents of this invention in enhancing bladder capacity and reducing voiding frequency.

I claim:

1. In a method of treating a patient for neuro-muscular incontinence, the step which comprises administering to said patient a thiol-S-(2-diethyl-aminoethyl)-ester compound selected from the group of trimethylacetyl-thio-S-(2-diethylaminoethyl)-ester, 1-cyclohexyl-1-phenylacetyl-thiol-S-(2-diethylaminoethyl)-ester, palmitoyl-thio-S-(2-diethylaminoethyl)-ester, 4-t-butyl-benzoyl-thiol-S-(2-diethylaminoethyl)-ester, phenylacetyl-thio-S-(2-diethylaminoethyl)-ester, 4-phenyl-butyryl-thio-S-(2-diethylaminoethyl)-ester, and 2-ethyl-butyryl-thio-S-(2-diethylaminoethyl)-ester.

2. The method defined in claim 1 wherein said ester is administered in a dosage of about 15 mg/kg.

3. The method defined in claim 1 wherein said ester is administered as a hydrochloride.

4. The method defined in claim 1 wherein said ester is further administered in a dosage to enhance bladder capacity.

5. The method defined in claim 1 wherein said ester is further administered in a dosage to provide moderate antidiuretic effect.

6. The method defined in claim 1 wherein said ester is further administered in a dosage to re voiding frequency.

7. The method defined in claim 1 wherein said ester is further administered in a dosage of 100–400 mg tablets.

8. The method defined in claim 1 wherein said ester is further administered in microspheres.

9. The method defined in claim 1 wherein said ester is further administered by intravenous injection.

10. The method defined in claim 1 wherein said ester compound is trimethylacetyl-thio-S-(2-diethylaminoethyl)-ester.HCl.

11. The method defined in claim 1 wherein said ester compound is 1-cyclohexyl-1-phenylacetyl-thiol-S-(2-diethylaminoethyl)-ester.HCl.

12. The method defined in claim 1 wherein said ester compound is palmitoyl-thio-S-(2-diethylaminoethyl)-ester.HCl.

13. The method defined in claim 1 wherein said ester compound is 4-t-butyl-benzoyl-thiol-S-(2-diethylaminoethyl)-ester.HCl.

14. The method defined in claim 1 wherein said ester compound is phenylacetyl-thio-S-(2-diethylaminoethyl)-ester.HCl.

15. The method defined in claim 1 wherein said ester compound is 4-phenyl-butyryl-thio-S-(2-diethylaminoethyl)-ester.HCl.

16. The method defined in claim 1 wherein said ester compound is 2-ethyl-butyryl-thio-S-(2-diethylaminoethyl)-ester.HCl.

* * * * *

UNITED STATES PATENT AND TRADEMARK OFFICE
CERTIFICATE OF CORRECTION

PATENT NO. : 5,130,336
DATED      : July 14, 1992
INVENTOR(S): William M. Davis

It is certified that error appears in the above-identified patent and that said Letters Patent is hereby corrected as shown below:

In columns 7 and 8, in Table 3, under the subheading "$\pm$ SE", the first line, please change ".47" to --.57--.

In column 15, line 2 of Claim 6, please change "re" to --reduce--.

Signed and Sealed this

Twenty-ninth Day of June, 1993

Attest:

MICHAEL K. KIRK

Attesting Officer    Acting Commissioner of Patents and Trademarks